United States Patent [19]

Lyssy

[11] Patent Number: 5,138,870
[45] Date of Patent: Aug. 18, 1992

[54] APPARATUS FOR MEASURING WATER VAPOR PERMEABILITY THROUGH SHEET MATERIALS

[76] Inventor: Georges H. Lyssy, Rotfluhstrasse 87, CH-8702 Zollikon, Switzerland

[21] Appl. No.: 716,727

[22] Filed: Jun. 17, 1991

Related U.S. Application Data

[63] Continuation-in-part of Ser. No. 550,756, Jul. 10, 1990, abandoned.

[30] Foreign Application Priority Data

Jul. 10, 1989 [CH] Switzerland .................. 02561/89

[51] Int. Cl.⁵ .................. G01N 15/08; G01N 5/02
[52] U.S. Cl. ........................ 73/38; 73/29.01; 73/76
[58] Field of Search ............... 73/76, 29.01, 29.05, 73/38

[56] References Cited

U.S. PATENT DOCUMENTS

| | | | |
|---|---|---|---|
| 1,014,842 | 1/1912 | Muckenfuss | 73/38 |
| 2,047,765 | 7/1936 | Brabender | 73/76 |
| 2,269,569 | 1/1942 | Williams | 73/76 |
| 2,828,623 | 4/1958 | Benedict | 73/76 |
| 3,144,765 | 8/1964 | Wollner | 73/76 |
| 3,286,509 | 11/1966 | Gluckman et al. | 73/38 |
| 3,446,060 | 5/1969 | Venezky et al. | 73/76 |
| 3,760,773 | 9/1973 | Christensen | 73/38 |
| 3,902,068 | 8/1975 | Wood | 73/38 |
| 3,973,431 | 8/1976 | Ginhoux et al. | 73/76 |
| 3,994,156 | 11/1976 | Koster | 73/76 |
| 4,142,403 | 3/1979 | Lohnes et al. | 73/76 |
| 4,168,623 | 9/1979 | Thomas, Jr. | 73/76 |
| 4,581,921 | 4/1986 | Gillespie et al. | 73/38 |
| 4,838,705 | 6/1989 | Byers, Jr. et al. | 73/76 |

FOREIGN PATENT DOCUMENTS

| | | | |
|---|---|---|---|
| 1063832 | 8/1959 | Fed. Rep. of Germany | 73/38 |
| 0044825 | 4/1981 | Japan | 73/76 |
| 0067848 | 4/1982 | Japan | 73/76 |
| 0165038 | 9/1983 | Japan | 73/76 |
| 0643790 | 1/1979 | U.S.S.R. | 73/76 |
| 0794427 | 2/1981 | U.S.S.R. | 73/76 |
| 1045083 | 9/1983 | U.S.S.R. | 73/38 |

*Primary Examiner*—Allan N. Shoap
*Assistant Examiner*—Diego F. F. Gutierrez
*Attorney, Agent, or Firm*—Speckman & Pauley

[57] ABSTRACT

An apparatus for measuring the water vapor permeability of sheet materials such as films, foils, paper and cardboard, under adjustable constant measuring conditions. A lid having an air inlet opening and an outlet opening is attached on a cup containing water in a vapor and airtight manner. A sheet material, its circumferential border sealingly held between the rims of the cup and lid, separates the water in the cup from the lid. An absorption member containing a moisture-absorbent material is in communication with the outlet opening. A blower in communication with the air inlet opening aspirates air through an air dryer and blows the resulting dry air into the sealed cup containing the sheet material, the permeability of which is to be measured.

12 Claims, 2 Drawing Sheets

APPARATUS FOR MEASURING WATER VAPOR PERMEABILITY THROUGH SHEET MATERIALS

CROSS-REFERENCE TO RELATED APPLICATION

This application is a continuation-in-part of my earlier filed application, Ser. No. 07/550,756, filed on Jul. 10, 1990, now abandoned.

BACKGROUND OF THE INVENTION

1. Field of the Invention

This invention relates to an apparatus for measuring the water vapor permeability through sheet materials such as films, foils, paper or cardboard, under adjustable constant measuring conditions.

2. Description of the Prior Art

For testing the water vapor permeability of plastic foils, paper or cardboard, the German Standard DIN 53122 stipulates stretching the sample to be tested in a water vapor-tight manner over a dish filled with an absorption medium, providing a stream of humid air containing a known percentage of relative humidity over the sample and determining the weight increase of this dish by weighing.

The disadvantage of this method is that the weight increase is based on weighing the dish, exactly to the nearest milligram, which itself weighs some hundreds of grams. Not only is such weighing cumbersome, because the dish must be taken out of the apparatus, but it also leads to measurement errors due to the large difference between the weight of the dish, typically on the order of 500 grams, and the accuracy of the required measurement, namely to the nearest milligram, or preferably, the nearest tenth of a milligram.

SUMMARY OF THE INVENTION

It is, therefore, one object of this invention to simplify the measuring of the water vapor penetration. This object is achieved in accordance with this invention in an apparatus which permits a direct measuring of the amount of water vapor which has, under adjustable constant measuring conditions, penetrated a sheet material such as a film, foil, paper or cardboard.

The apparatus, in accordance with one embodiment of this invention, is a water tight container comprising a cup containing water over which the sheet material is stretched and a lid sealingly attachable to the cup such that a seal is effected on the circumferential border of the sheet material. The lid has an air inlet opening through which dry air is introduced into the container and an air outlet opening in communication with a removable absorption member containing a moisture-absorbent material into which moisture-laden air from the container flows. To determine the water vapor permeability of the sheet material, the absorption member, weighing on the order of 50 grams, but in any event, substantially less than the absorption medium-containing dish of the known prior art, is weighed before and after the test to the nearest milligram, and preferably, to the nearest tenth of a milligram. Due to the small difference between the weight of the absorption member and the accuracy of the measurement, compared to the known prior art, the measurement error is substantially smaller. In addition, the equipment required to measure the weight of the smaller weight absorption member to the accuracy required is significantly less expensive than the equipment required to measure the weight of the significantly heavier dish of the known prior art.

The measurement conditions, in particular, the amount of air which is flowing over the sample, and the temperature, are kept constant, because the permeation of water vapor depends to a large extent on the temperature. On the other hand, tests have shown that the results of measurements are within reasonable limits independent of the air flow. An embodiment of an apparatus for measuring the permeability according to this invention is shown in the attached drawings in a simplified manner.

DESCRIPTION OF THE PREFERRED EMBODIMENTS

Figure 1:
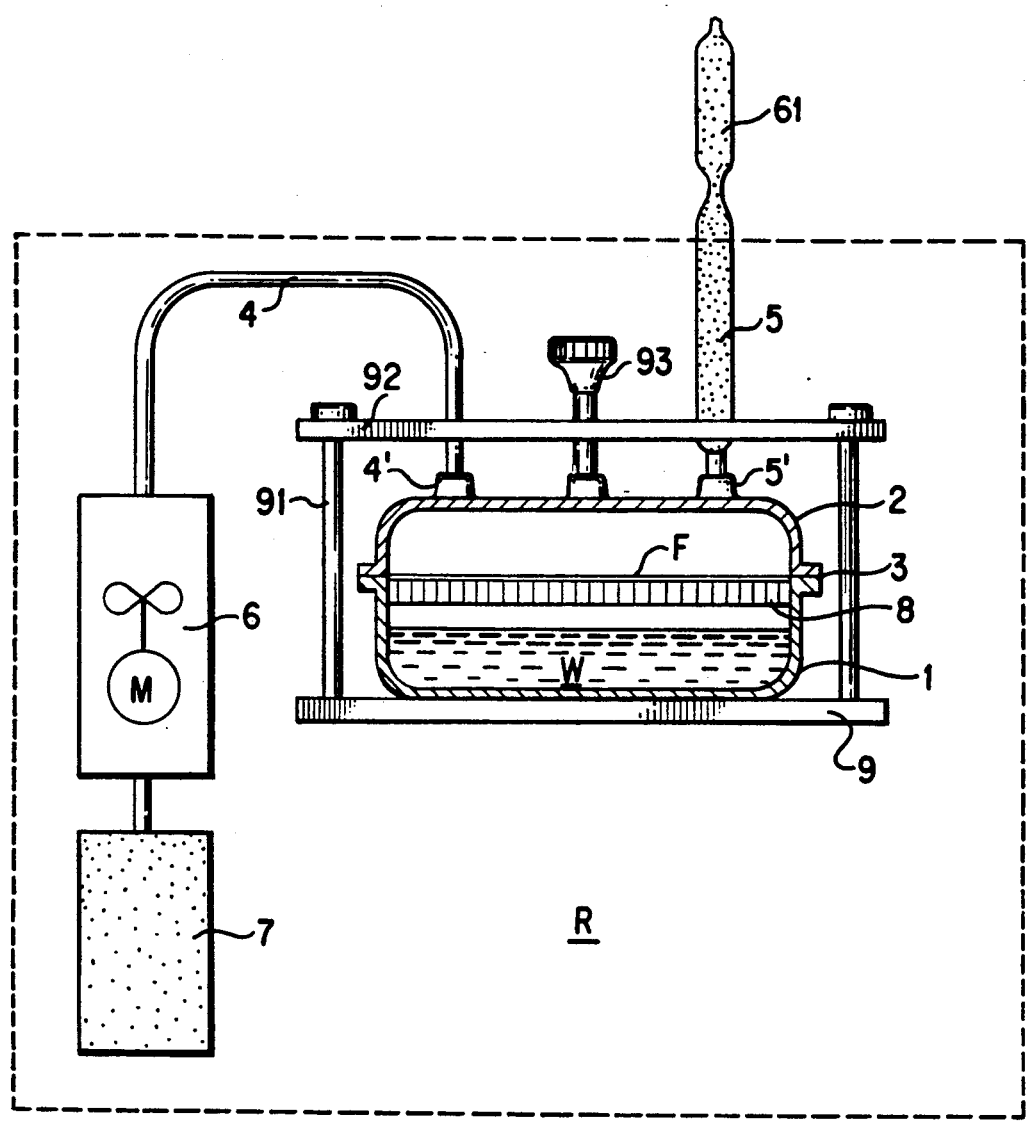
FIG. 1 is a schematic diagram of a testing apparatus for measuring the water permeability of a sample in accordance with one embodiment of this invention.

A testing apparatus in accordance with one embodiment of this invention is shown in FIG. 1. It comprises a cup 1 with a lid 2. The rim of the edge is provided with a seal 3 which tightly seals the film, foils, paper or cardboard on both sides. The lid 2 has an air inlet opening 4', to which a hose 4 is connected, through which a stream of dry air is introduced into the lid 2. Special attention should be given to make the hose 4 of a material impermeable to water vapor. The use of a metallic hose or a small metal pipe is preferred.

The lid 2 also has an air outlet opening 5', on which is positioned an absorption member 5 through which the air escapes. The absorption member 5 is filled with a moisture-absorbent material, for example, silica gel crystals or molecular sieves, so that it remains permeable to air. In accordance with one embodiment of this invention, the stream of dry air which enters the apparatus through the hose 4 is generated by blower 6, which aspirates ambient air through a silica gel air dryer 7.

The seal 3 between the cup 1 and the lid 2 sealingly holds the circumferential border of sheet material F, such as film, foil, paper or coated cardboard, the permeability of which is to be measured. A water vapor permeable support element 8 supports sheet material F. The cup 1 contains water W, the surface of which should be below the support element 8.

Figure 1A:
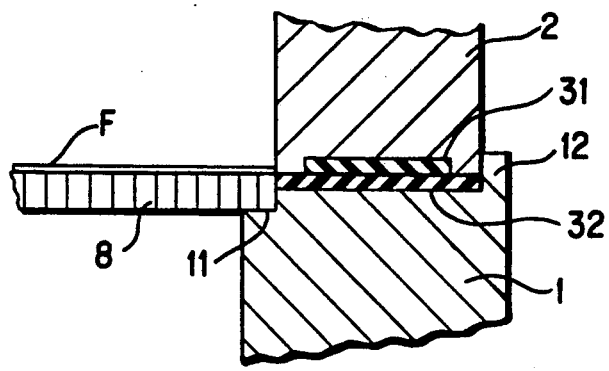
FIG. 1a is an enlarged view of the seal element of the testing apparatus shown in FIG. 1.

FIG. 1a shows details of the seal 3 in an enlarged view. The circumferential rim of the lid 2 has a groove holding a flat gasket 31. The circumferential rim of the cup 1 has a groove 11 holding the supporting element 8 and which is provided with a flat gasket 32. The outer side of the rim has an upstanding ridge 12 for centering the gasket 32, the foil F and the lid 2.

The cup 1 and lid 2 are sealingly pressed one upon the other by help of outward means for compressing comprising a base plate 9, two pullrods 91, a yoke 92 and a screw 93.

Figure 2:
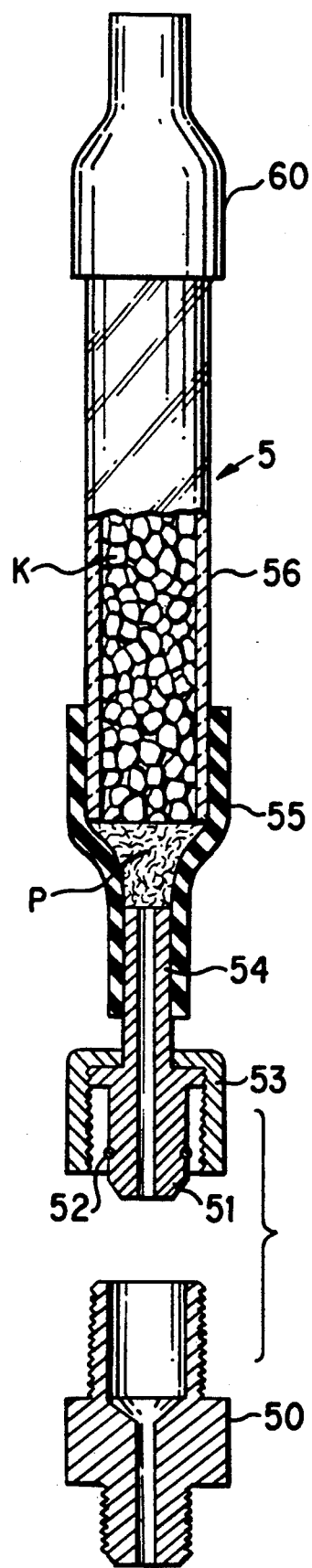
FIG. 2 is a cross-sectional diagram of a removable absorption member attached to the apparatus with an associated connecting nipple.

The air-permeable absorption member 5 containing the silica gel crystal is shown in an enlarged view in FIG. 2. For taking the measurements, it is an important feature of this invention that the absorption member 5 can be easily removed from the lid 2, weighed at set intervals and then put back on the lid. For this purpose, the member 5 comprises a coupling with a nipple 50 fixed on the lid 2 and having a bore into which a hollow tang 51 can be inserted. O-ring 52 seated in a groove in hollow tang 51 provides a seal and a union nut 53 provides the support of the absorption member 5 on the nipple 50. The hollow tang 51 converts into a hose connector 54, on which a rubber cuff 55, which diverges towards the top, as shown, has been placed and the widened part of which grips a glass tube 56. The glass tube 56 is filled with moisture-absorbent material, preferably, silica gel crystals, K, and provided with a cuff 60 at the top. Plugs P of material permeable to water vapor, for example, a plastic filter or synthetic, non-hygroscopic cotton wool, are disposed on the top and bottom, so that crystals cannot fall out.

Measurement must be taken at a constant temperature in order to obtain usable measuring results, because the release of water vapor depends to a large extent on the temperature. In FIG. 1, in accordance with one embodiment of this invention, the apparatus as a whole is positioned in a thermostatically controlled chamber R, which is indicated by dashed lines.

To measure the water vapor permeability of sheet materials such as films, foils, paper or cardboard using the apparatus of this invention, first, the absorption member 5 is exactly weighed before the test begins.

Motor M of the blower 6 is switched on so that air sucked through the air dryer 7 flows into the lid 2 over the surface of the sheet material F, the water vapor permeability of which is to be measured. During the entire duration of the test, the temperature is maintained constant.

After certain time intervals, the pump is switched off and the member 5 is taken off from the lid 2 and weighed again.

The increase of weight of the absorption member gives an indication of the water vapor permeability of the sheet material F in milligrams per unit of time. Because the surface enclosed by the clamping edge 3 is known, the permeability of sheet material F can be converted to the conventional unit of permeability of $g/m^2 d$ (grams per square meter per day).

Instead of placing the entire apparatus into a thermostatically controlled chamber R, as shown in FIG. 1, it is also possible to control the temperature of the apparatus, that is, cup and lid themselves, in accordance with another embodiment of this invention, thermostatically by cooling/heating conduits positioned in the walls.

Tests of the apparatus have shown that measuring results are obtained using this apparatus which either coincide with the known, much more complicated methods, or are even more accurate. In a conventional method, it is required to weigh the test object itself for each weighing, and to remove it each time from the test chamber for this purpose.

The measuring process using the apparatus of this invention is so accurate that, as tests have shown, with the use of a simple plastic tube 4, water vapor from the surroundings diffuses through the tube wall. Thus, it is preferred to employ a metallic hose or a metallic tube.

An additional factor which can influence the accuracy of the measurement is that it is possible for water vapor from the surrounding air to be absorbed by the hygroscopic material of the member 5. This adverse factor can be removed, in accordance with another embodiment of this invention, by placing a second absorption member 61, constructed similar to the member 5, downstream of the latter, which prevents reverse absorption of water vapor from the ambient air.

I claim:

1. An apparatus for measuring the water vapor permeability of a sheet material under adjustable constant measuring conditions comprising:
   a cup (1) containing water (W);
   a lid (2) attachable on said cup (1) in a vapor and airtight manner, said lid (2) having an air inlet opening (4') and an outlet opening (5');
   a seal (3) disposed in a circumferential cup rim of said cup (1) and a circumferential lid rim of said lid (2), said seal (3) sealingly holding a circumferential border of said sheet material;
   a primary absorption member (5) capable of transmitting a fluid in communication with said outlet opening (5'), said primary absorption member (5) containing a moisture-absorbent material;
   a blower (6) in communication with said air inlet opening (4'); and
   an air dryer (7) in communication with said blower (6), whereby air is aspirated by said blower (6) through said air dryer (7) and introduced into said air inlet opening (4').

2. An apparatus in accordance with claim 1, wherein a first hose connector is connected to said lid (2) in communication with said air inlet opening (4').

3. An apparatus in accordance with claim 1, wherein a nipple (50) having a longitudinal bore is connected to said lid (2) in communication with said outlet opening (5'), said primary absorption member (5) removably connected to said nipple (50) by a union nut (53).

4. An apparatus in accordance with claim 1, wherein said primary absorption member (5) comprises a tubular member (56), a first cuff (60) secured to one end of said tubular member (56), a second cuff (55) secured to the other end of said tubular member (56), said second cuff (55) converging to receive a second hose connector (54), said second hose connector (54) in communication with said tubular member (56) converting to a hollow tang (51) having a circumferential groove, a sealing member (52) seated in said circumferential groove, said hollow tang (51) insertable into a nipple (50) having a longitudinal bore, said nipple (50) connected to said lid (2) in communication with said outlet opening (5').

5. An apparatus in accordance with claim 1, wherein said seal (3) comprises said circumferential lid rim having a lid groove into which a first flat gasket (31) is inserted, and said circumferential cup rim having a cup groove (11) supporting a water vapor permeable support element (8) beneath said sheet material and into which a second flat gasket (32) is inserted.

6. An apparatus in accordance with claim 5, wherein an outer side of said circumferential cup rim has an upstanding ridge (12).

7. An apparatus in accordance with claim 1, wherein compressing means for compressing sealingly press said lid (2) and said cup (1) together.

8. An apparatus in accordance with claim 7, wherein said compressing means for compressing comprises a base plate (9), a plurality of pullrods (91), a yoke (92), and a screw (93).

9. An apparatus in accordance with claim 1, wherein a hose (4) connects said blower (6) to said air inlet opening (4'), said hose (4) being made of a material impermeable to water vapor.

10. An apparatus in accordance with claim 1, wherein said moisture-absorbent material is one of silica gel crystals and a molecular sieve.

11. An apparatus in accordance with claim 1, wherein said cup (1), said lid (2), said blower (6), said air dryer (7), and at least a portion of said primary absorption member (5) are enclosed in a thermostatically controlled chamber (R).

12. An apparatus in accordance with claim 1, wherein a secondary absorption member (61) is disposed downstream of said primary absorption member (5) and in communication with said primary absorption member (5).

* * * * *